(12) United States Patent
Ikeda

(10) Patent No.: US 6,538,831 B1
(45) Date of Patent: Mar. 25, 2003

(54) METHOD AND APPARATUS FOR USING RECORDING AND READING MEDICAL INFORMATION AND IMAGE INFORMATION WITH DIGITAL AUDIOTAPE

(75) Inventor: Shigeyuki Ikeda, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 08/336,690

(22) Filed: Nov. 7, 1994

Related U.S. Application Data

(63) Continuation of application No. 08/073,296, filed on Jun. 7, 1993, which is a continuation of application No. 07/242,124, filed on Sep. 9, 1988.

(30) Foreign Application Priority Data

Sep. 11, 1987 (JP) .......................................... 62-226416
Sep. 11, 1987 (JP) .......................................... 62-226417

(51) Int. Cl.⁷ .............................. G11B 5/00; G11B 5/09
(52) U.S. Cl. .............................................. 360/32; 705/4
(58) Field of Search ........................... 705/52, 2, 3, 4, 705/57; 702/189; 386/46, 109, 125, 75, 104, 64; 348/301, 74, 75, 77; 360/15, 39, 32; 711/115; 704/500, 270; 380/53, 59; 381/124; 375/372; 600/407, 425; 345/419, 420, 424, 606; 707/204, 1, 3; 128/920; 235/375; 358/403, 404

(56) References Cited

U.S. PATENT DOCUMENTS

| | | | | |
|---|---|---|---|---|
| 4,530,048 A | * | 7/1985 | Proper | 360/15 |
| 4,611,247 A | * | 9/1986 | Ishida et al. | 128/653 R |
| 4,737,912 A | * | 4/1988 | Ichikawa | 364/413.02 |
| 4,812,924 A | * | 3/1989 | Fukami et al. | 360/32 |
| 4,872,070 A | * | 10/1989 | Cooper et al. | 360/15 |

OTHER PUBLICATIONS

*The microcomputer in the Dental Office: a new Diagnostic Aid* by Van Der Stelt, International Dental Journal, Jun. 1985 (abstract only).*
*From the Physician's Viewpoint* by Joe Wadlinger, Physicians & Computers v.3, n.6, Oct. 1985 (abstract only).*
*Computer Applications in Obstetrics* reported in the American Journal of Obstetrics and Gynecology, May 1987 (abstract only).*
*Medical Computerized Clinical History: Our Experience over 2 Years* by R. Valdez et al., reported in *Revista Argentina de Dermatologia*, 1987 (abstract only).*
*Direct Entry of Patient Data to a Portable, Briefcase Computer Interface with Overview Medical Data Base at the Office* by S. R. Ash et al., Proceedings of the Seventh Annual Symposium on Computer Applications in Medical Care, 1984 (abstract only).*

* cited by examiner

Primary Examiner—Albert DeCady
Assistant Examiner—Guy Lamarre
(74) Attorney, Agent, or Firm—Antonelli, Terry, Stout & Kraus, LLP

(57) ABSTRACT

An apparatus for recording and reproduction of medical information comprises an input/output unit for inputting and outputting personal medical history information of individual patients, a processor for fetching digital personal medical history information supplied from the input/output unit and digital examination image information supplied externally and for applying a predetermined data processing to the two types of digital information, a digital audiotape (DAT) unit loaded with a DAT which is a magnetic cassette tape adapted for recording and reproduction of digitized audio signals, for recording and reproducing the digital information about personal medical history and examination images supplied from the processor on and from a recording medium in the form of the DAT, and a display unit for reproducing and displaying an examination image recorded in the DAT unit.

19 Claims, 10 Drawing Sheets

| IMAGING DATE | IMAGING UNIT | PART (NUMBER OF SHEETS) | DIAGNOSIS | HOSPITAL NAME |
|---|---|---|---|---|
| 1980.5.10 | CT | HEAD(10) | NP. | KASHIWA HP |
| 1981.3.1 | US | ABDOMEN(2) | NP. | TODAI HP |
| 1981.10.1 | X-RAY | CHEST(1) | NP. | TOKYO HP |

DATE, ID NUMBER, NAME, AGE UNIT, PART, NUMBER OF SHEETS AND SO ON

EXAMINATION IMAGES

FIG. 6

| DATE | ID NUMBER | NAME | AGE | UNIT | PART | NUMBER OF SHEETS |
|---|---|---|---|---|---|---|
| 88.4.1 | 1223 | TARO YAMADA | 29 | CT | HEAD | 10 |
| 4.2 | 1225 | HARUKO SUZUKI | 27 | MRI | ABDOMEN | 8 |
| 4.5 | 1230 | YOICHI HITACHI | 20 | X-RAY | CHEST | 1 |

F I G. 7
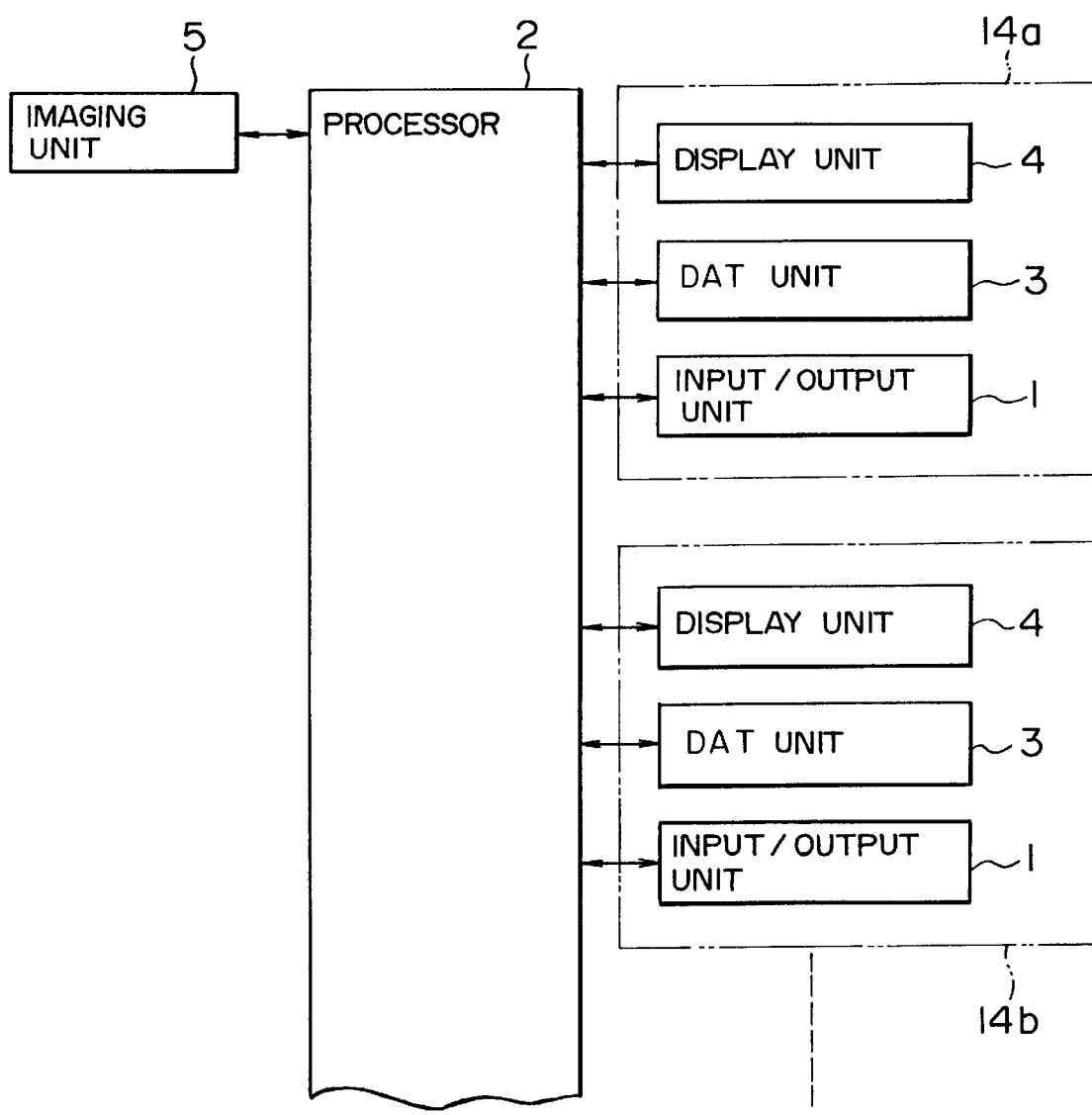

# METHOD AND APPARATUS FOR USING RECORDING AND READING MEDICAL INFORMATION AND IMAGE INFORMATION WITH DIGITAL AUDIOTAPE

This application is a continuation-in-part of application Ser. No. 08/073,296, filed on Jun. 7, 1993 which is a continuation of parent application Ser. No. 07/242,124, filed on Sep. 9, 1988.

BACKGROUND OF THE INVENTION

This invention relates to method and apparatus for using, recording and reading medical information and image information with digital audiotape and more particularly to medical information recording and reproducing which utilize a digital audiotape (DAT) unit to permit recording and reproduction of digital medical information and digital information representative of an examination image to and from a DAT.

Recently, advanced medical treatment and diagnosis techniques aided by an X-ray imaging unit, an X-ray computerized tomography (CT) unit, an ultrasonic diagnostic unit, a magnetic resonance imaging (MRI) CT (?) and the like have permitted a patient to take a systematic diagnostic and therapeutic treatment. In addition, the number of medical facilities such as hospitals has increased and hence efficient and secure diagnostic and therapeutic treatments have been attempted by exchanging information about therapeutic history and medicative history of individual patients between medical facilities. Under the circumstances, applicability of an IC card based on an IC or an optical card writable with a laser beam to a medium for recording the information about therapeutic and medicative histories of individual patients has hitherto been studied. The IC card is the same type as a cash card used with banks and incorporates a central processing unit (CPU), a memory and an input/output circuit. The memory has a storage capacity which can amount to about 30 to 64 K bytes. The optical card resembles the cash card but information is optically recorded using a laser beam. The recording capacity can amount to about 500 K bytes to 2 megabytes. When used for recording character information, the IC card and the optical card can record 30,000 to 64,000 characters and 500,000 to 2,000,000 characters, respectively, and their capacity proves to be sufficient for recording therapeutic and medicative histories of a single patient.

With recent progress of image diagnostic techniques, images taken by the X-ray imaging unit, X-ray CT unit, ultrasonic diagnostic unit, MRI CT unit and the like play an important role in conducting diagnosis and therapy of patients. This raises the need of providing a record of information of various examination images as above in the therapeutic history of individual patients. However, when the image is digitized for recording, a very great amount of digital data is generated. For example, in performing 16-bit digitizing of an X-ray film of 40 cm×35 cm, about 8 megabits (1 megabytes) per image frame are needed. Therefore, the recording capacity of the IC card is insufficient to record the image. Even with the optical card, its recording capacity is insufficient to record a plurality of sheets of image.

Thus, the IC card and optical card are sufficient only for recording therapeutic and medicative histories of individual patients but because of their insufficient recording capacity, they fail to record, along with the histories, examination images taken by various units. Accordingly, in actually conducting diagnosis and therapy in hospitals and medical facilities, a personal medical history such as therapeutic and medicative histories of individual patients can be taken out of the IC card or optical card but examination images can not be supplied therefrom, with the result that it is necessary to get the examination image separately. Therefore, sufficient diagnostic information can not be obtained rapidly. Under the circumstances, a patient is sometimes prevented from undergoing efficient diagnosis and therapy. In addition, even if a diagnostic part has been imaged in the past, the same part will sometimes be examined to obtain a duplicative examination image, thereby imposing an unnecessary load on a patient.

SUMMARY OF THE INVENTION

An object of this invention is to provide a method and apparatus for using, recording and reading medical information and image information with a digital audiotape which can solve the above conventional problems by using recently developed DAT as a recording medium.

According to the invention, the method thereof includes the steps of fetching digital medical information supplied from an input unit and digital examination image information supplied externally, applying a predetermined data processing to the two types of digital information in a processor, recording and reproducing the digital medical information and digital examination image information supplied from the processor on and from a recording medium in the form of the digital audio tape (DAT), and reproducing and displaying an examination image recorded on the DAT.

In the medical information recording and reproducing method as described above, no audio signal is digitized for recording and reproduction on and from the DAT by a DAT unit but the DAT is used as a recording medium of large capacity which directly records digital data externally supplied, whereby both the digital medical information and examination image information of individual patients can be stored systematically on the DAT.

BRIEF DESCRIPTION OF THE DRAWINGS

FIG. 5 is a diagram showing another example of a data format recorded on the DAT.

FIG. 6 is a diagram showing an example of the contents of medical information in the FIG. 5 format.

FIG. 7 is a block diagram of a medical information recording and reproducing apparatus according to another embodiment of the invention.

DESCRIPTION OF THE PREFERRED EMBODIMENTS

The invention will now be described by way of example with reference to the accompanying drawings.

Figure 1:
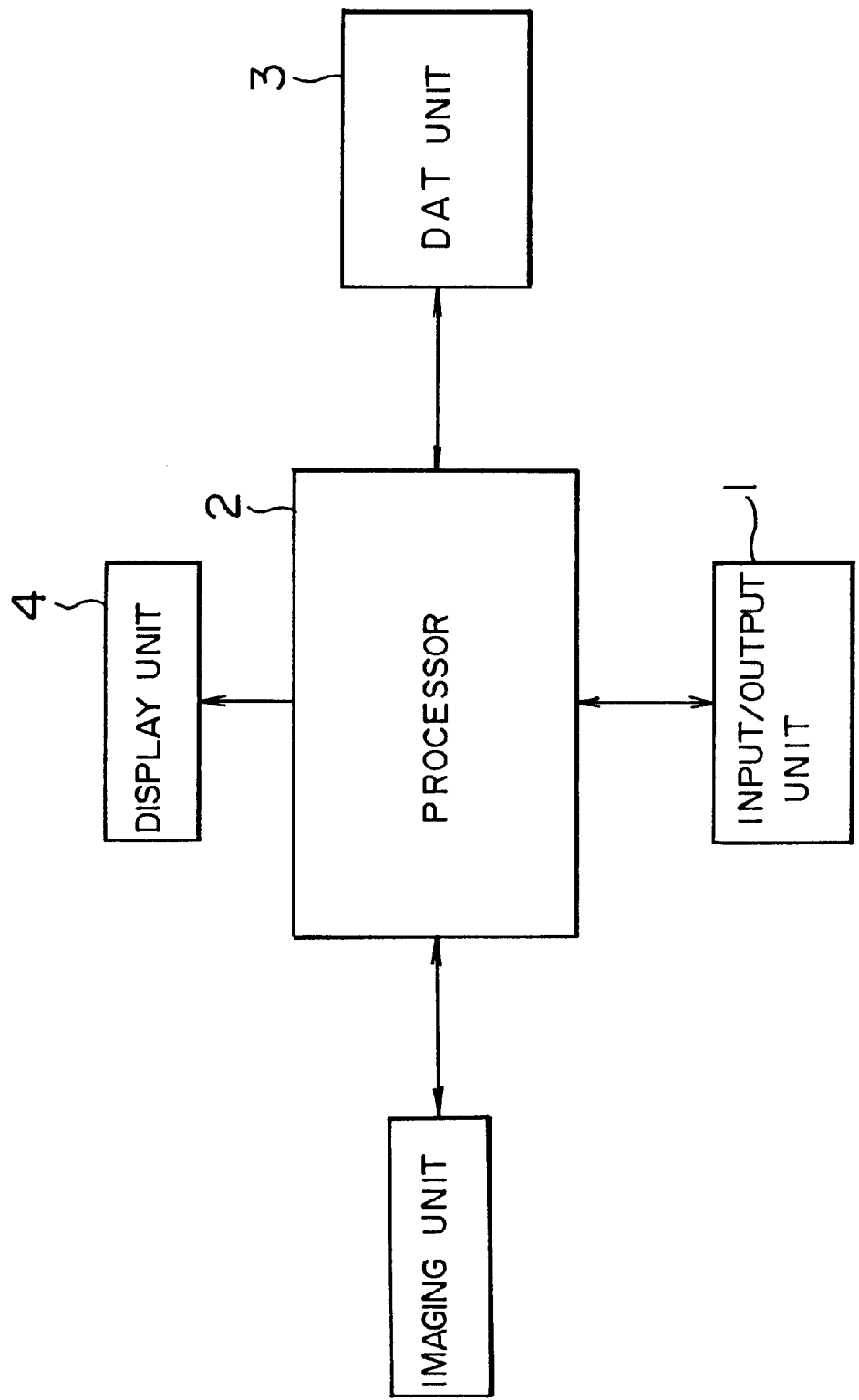
FIG. 1 is a block diagram of a medical information recording and reproducing apparatus according to an embodiment of the invention.

Referring now to FIG. 1, there is illustrated, in block form, an apparatus for recording and reproducing medical information according to an embodiment of the invention. The recording and reproducing apparatus is operable to record and reproduce personal medical history information of individual patients and includes, as shown in FIG. 1, an input/output unit 1, a processor 2, a DAT unit 3 and a display unit 4. In FIG. 1, reference numeral 5 designates an imaging unit for production of various examination images, such as an X-ray imaging unit, an X-ray CT unit, an ultrasonic diagnostic unit, an MRI CT unit and the like.

The input/output unit 1 is adapted to input/output information about personal medical history such as therapeutic and medicative histories of individual patients in the form of digital character information and it comprises, for example, a character keyboard and a monitor. The processor 2 fetches not only the digital personal medical information delivered out of the input/output unit 1, for example, identification (ID) information indicative of patient's name, age, sex and the like, therapeutic history information and medicative history information but also digital examination image information delivered out of the external imaging unit 5, and converts all of the digital information into a data format matching the DAT unit.

The DAT unit 3 is adapted to systematically record and reproduce digital information about personal medical history and examination image transferred from the processor 2 on and from a recording medium in the form of a DAT. The DAT is a recently developed magnetic cassette tape adapted for recording and reproducing of digitized audio signals and because of its ability to record and reproduce sound of high quality, it is principally used for music. In the case of the DAT, it has so large a capacity that a roll of magnetic tape built in a compact cassette of, for example, 54 mm×73 mm×10.5 mm has a large capacity of about 1.4 gigabytes when 16-bit digitizing is performed at, for example, 48 KHz sampling, and it has an error rate of $10^{-15}$, indicating that the DAT is comparable or superior to the magnetic disc from the standpoint of reduction in code error. Incidentally, when various examination images necessary for image diagnosis in the field of medical treatment, for example, X-ray images, X-ray CT images, ultrasonic diagnosis images and MRI CT images are digitized, they have a data capacity which corresponds to about 8 megabits (1 megabytes) per image frame when an X-ray film of, for example, 40 cm×35 cm is subjected to 16-bit digitizing. Other examination images have a data capacity which is almost comparable to the above. Therefore, the large capacity of about 1.4 gigabytes of the DAT is sufficient to store a great number of. digital images.

Figure 2:
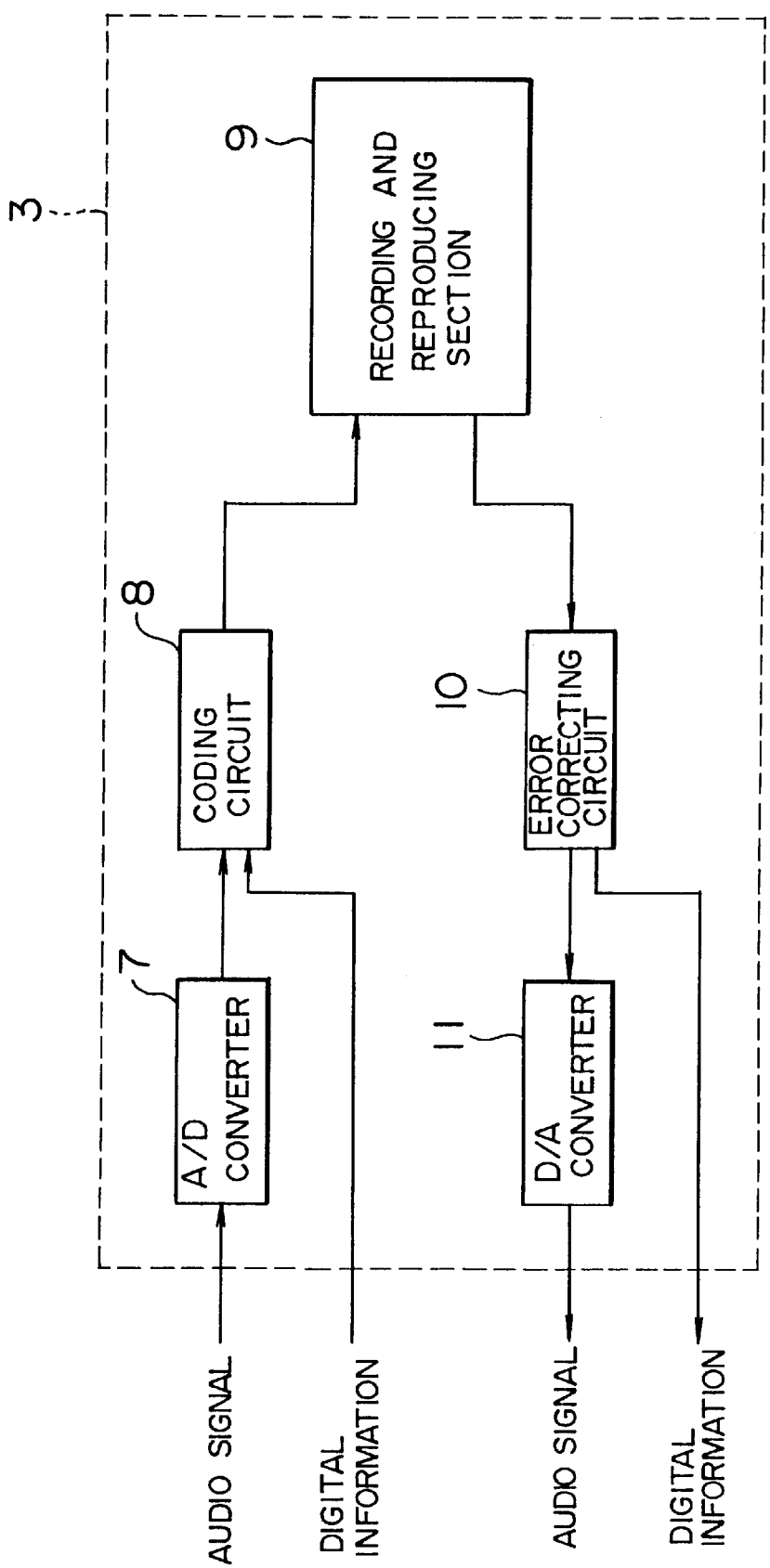
FIG. 2 is a block diagram showing details of the essential block in FIG. 1.

The DAT used as the recording medium is loaded on the DAT unit 3 the internal construction of which is illustrated, in block form, in FIG. 2. The DAT unit has, on the data input side, an A/D converter 7 for fetching an audio signal and performing, for example, 16-bit digitizing to convert the fetched audio signal into digital information, and a coding circuit 8 for converting the digital information into a data format matching magnetic recording and for adding an error correcting code used to correct an error code occurring during reproduction. An output data signal from the coding circuit 8 is applied to a recording and reproducing section 9 comprised of a tape running system and a recording/reproducing head. The output data signal is recorded on the recording medium in the form of the DAT loaded in the section 9. The DAT unit 3 has, on the data output side, an error correcting circuit 10 for inverse converting the data read out of the DAT under the direction of the recording and reproducing section 9 into the original information and correcting the code error by using the error correcting code, and a D/A converter 11 for receiving an output data signal from the error correcting circuit 10 and converting the data signal into an output audio signal. The coding circuit 8 and error correcting circuit 10 respectively have an input port and an output port through which digital information is directly exchanged between the DAT unit 3 and the external input/output device, for example, the processor 2 shown in FIG. 1. With the input and output ports provided, the A/D converter 7 and D/A converter 11 may be omitted.

Figure 3:
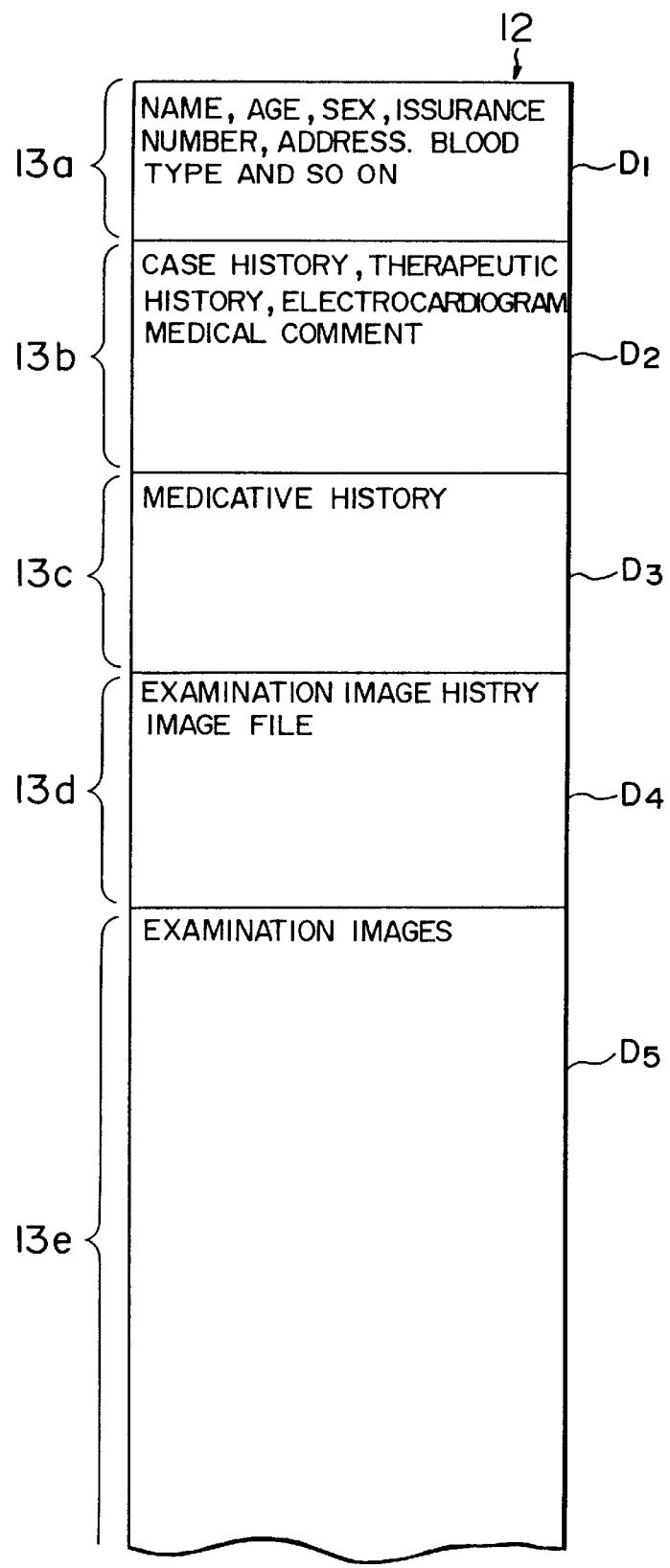
FIG. 3 is a diagram showing an example of a data format recorded on a DAT in accordance with the invention.

In particular, in accordance with the present invention, no audio signal is digitized by the A/D converter 7 and recorded on the DAT loaded in the recording and reproducing section 9 of the DAT unit 3 but the input port provided in the coding circuit 8 and the output port provided in the error correcting circuit 10 are utilized so that digital information about therapeutic and medicative histories and digital information about various examination images of individual patients delivered out of the processor 2 shown in FIG. 1 may be inputted through the input port to the DAT unit 3 and directly recorded on the DAT and that the digital information about the personal medical history and examination images recorded on the DAT may be read out thereof and sent through the output port directly to the processor 2 shown in FIG. 1. An example of a data format recorded on the DAT is shown in FIG. 3. With this data format, ID information $D_1$ indicative of name, age, sex, insurance number, address and blood type of a patient is recorded on the head area 13a on the DAT, information $D_2$ about a personal medical history including a case history, a therapeutic history, an electrocardiogram and medical comment is recorded on a subsequent area 13b, information $D_3$ about a personal medical history particularly including a medicative history is recorded on a further subsequent area 13c, information $D_4$ about an examination image history and an image file is recorded on a further subsequent area 13d, and information $D_5$ about various examination images is recorded on the final area 13e. Accordingly, when the head area 13a to the fourth area 13d of the DAT are read during reproduction, almost all of data including the ID information $D_1$, personal medical history information $D_2$, medicative history information $D_3$ and examination image history information $D_4$ can be obtained. During diagnosis, a necessary examination image may be read out of the final area 13e, as necessary.

The areas 13a to 13d are respectively allocated with 100 K bytes and 100,000 characters each represented by a 8-bit code can be recorded on each area. Because of about 1.4 gigabytes of the DAT, most of the DAT is allocated to the area 13e for recording of examination images. Accordingly, reading of the areas 13a to 13d can be completed within a few seconds.

Figure 4:
FIG. 4 is a diagram showing an example of specific contents of an area D4 in FIG. 3.

Specifically, the contents of the examination image history and image file recorded on the area 13d of FIG. 3 is represented by imaging date, imaging unit, imaged part, number of imaged sheets and the like as shown in FIG. 4 and when read out of the area 13d, an image representative of the contents is displayed on the display unit 4 as shown in FIG. 4.

Displayed on the lefthand margin of the image shown in FIG. 4 is a cursor 41 which can be moved vertically to designate a desired item. Image information corresponding to the designated item is read out of the examination image area 13e and displayed on the display unit 4.

The examination images recorded in the DAT unit 3 are reproduced and displayed on the display unit 4 shown in FIG. 1 which is, for example, a CRT display.

The apparatus for recording and reproduction of personal medical information constructed as above is used in a manner as will be described below. Individual patients have and personally manage cassette DAT's in which digital information about personal medical history and examination images of individual patients is systematically stored. When a patient with a cassette DAT visits a hospital to undergo diagnosis and therapy, the patient loads the cassette DAT on the DAT unit 3 of the recording and reproducing apparatus in accordance with the invention, so that information about all of personal medical histories of the patient prepared till then is read out and outputted to the input/output unit 1. Then, diagnosis and therapy are conducted by considering the personal medical history information and reading and displaying various examination images on the display unit 4 as necessary. When necessary diagnosis and therapy are terminated, newly prepared digital information about personal medical history and examination images is recorded on the corresponding area of the DAT and the cassette DAT is again placed under personal management of the patient.

The foregoing embodiment of FIG. 1 has been described by referring to the DAT which belongs to individual patients but the invention is not limited thereto. For example, when the imaging unit sequentially images different patients, a DAT loaded on the DAT unit to record image information is not exchanged each time a patient changes to another, in order that image information about sequentially obtained images can be recorded on the same DAT. In this case, a single DAT remains loaded on the DAT unit during a predetermined period of time, for example, for a day, a week or a month and at the expiration of the period of time the DAT is exchanged with new one. Obviously, exchange of a DAT may be effected each time recorded image information fills up the recording capacity of the DAT.

When a single DAT is used for different patients, the recording format of the DAT has, as shown in FIG. 5, an area for recording medical information including imaging date, ID number, name, age, imaging unit, imaged part, number of imaged sheets and so on and another area for recording examination images corresponding to respective items of the medical information which are displayed on the display unit in a format as shown in FIG. 6. As described in connection with FIG. 4, the image information may be itemized and an item designated by a cursor on the lefthand margin may be read and executed.

FIG. 7 illustrates, in block form, a medical information recording and reproducing apparatus according to another embodiment of the invention. The apparatus of this embodiment has DAT's belonging to individual patients and is actually used in hospitals. In this embodiment, a processor 2 is installed at the center of a hospital and consulting rooms 14a, 14b, - - - are each provided with an input/output unit 1, a DAT unit 3 and a display unit 4. With this construction, data prepared in the respective consulting rooms 14a, 14b, - - - can be processed on time sharing procedure to realize an overall medical image managing system in which personal medical history and various examination images are totally utilized for diagnosis and therapy.

Figure 8:
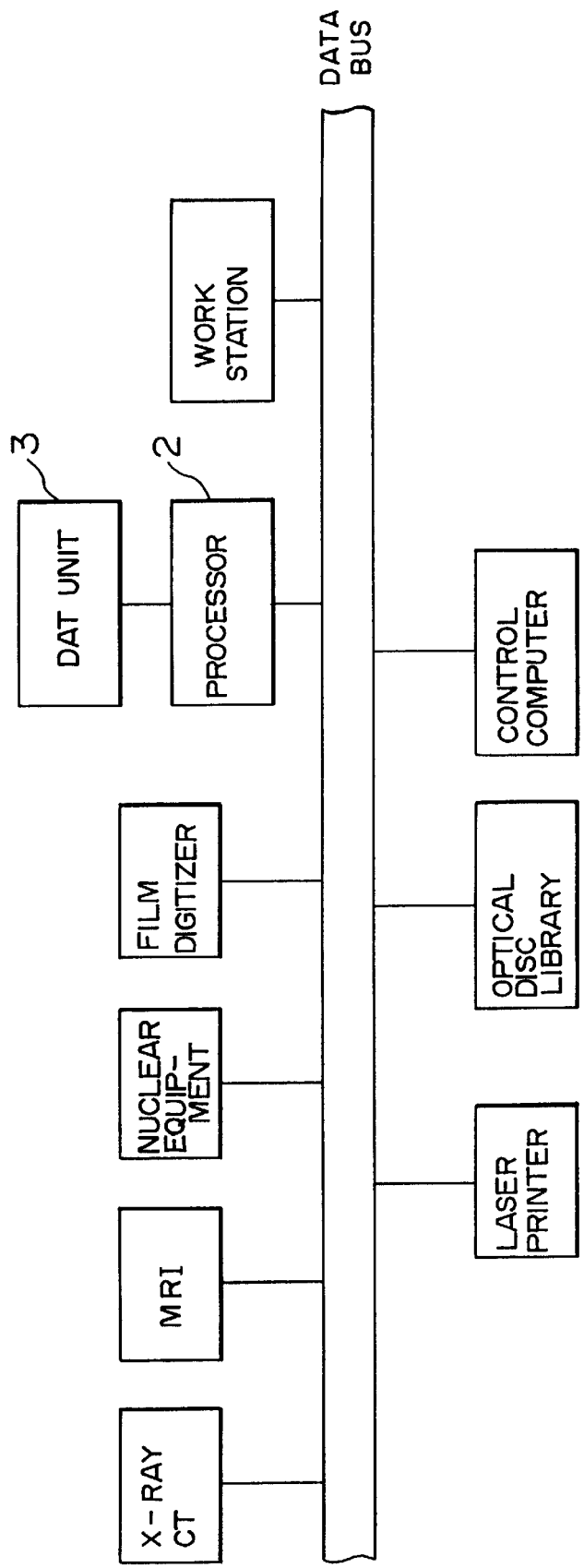
FIG. 8 is a block diagram showing an instance in which the invention is applied to an existing picture archiving and communications system.

Referring to FIG. 8, the invention can be practiced by connecting a DAT unit to a picture archiving and communications system (PACS) as described in "New Medical Treatment", September, 1986, pp. 66–69.

An existing PACS comprises, as shown in FIG. 8, an X-ray CT unit, an MRI CT unit, a nuclear equipment and a film digitizer which provide image information output signals, an optical disc library for recording the image information output signals, a work station operable to generate various commands and read and display information, a laser printer for reading the image information recorded on the optical disk library so as to obtain a hard copy, and a control computer for controlling the above units. All of the units are coupled together by a data bus. In applying the present invention to the PACS, a DAT unit 3 is coupled to the data bus through a processor 2. The FIG. 8 apparatus constructed as above can operate similarly to the apparatus of FIGS. 1 and 7.

The processor 2 used in the embodiments of the invention shown in FIGS. 1, 7 and 8 operates as will be described below.

Figure 9:
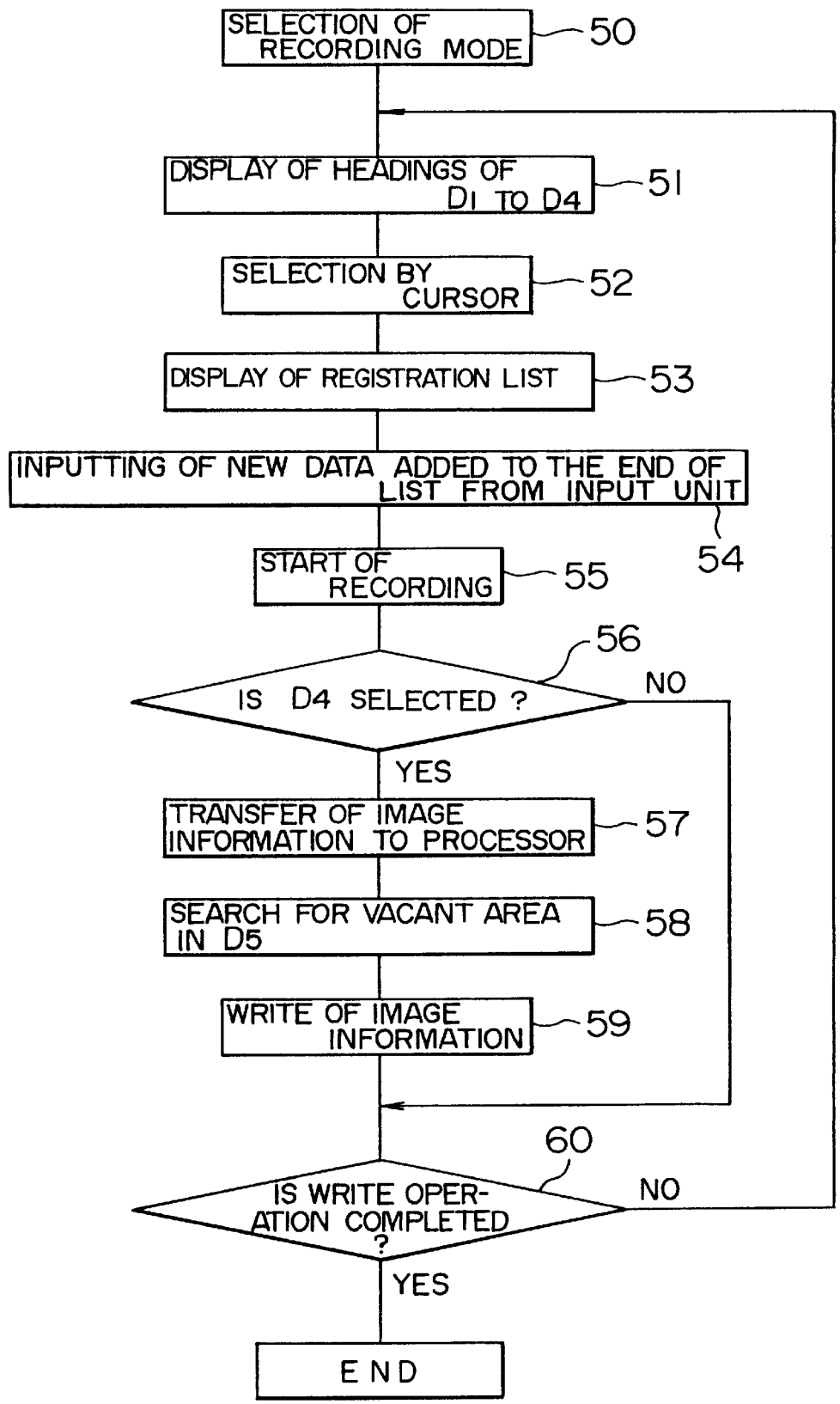
FIG. 9 is a flow chart for explaining the operation of the recording mode in accordance with the invention.

When the medical information from the input/output unit 1 and the image information from the imaging unit 5 are recorded on the DAT, the processor 2 operates in accordance with an operational flowchart shown in FIG. 9. Referring to FIG. 9, when the recording mode is first selected by the input/output unit 1 in step 50, the headings of the four kinds of medical information $D_1$ to $D_4$ are displayed on the display unit 4 in step 51. In step 52, the operator moves the cursor to select and designate one kind of medical information having the contents which the operator wishes to input. Then, in step 53, a registration list recorded on the DAT in respect of the selected medical information is displayed on the display unit 4. In step 54, an item to be newly recorded is added to the end of the read-out registration list by inputting the new item from the input/output unit 1 and displayed on the display unit 4. Subsequently, in step 55, the DAT unit 3 is operated to record the input item on the DAT at the end of the recording area corresponding to the designated medical information. It is decided in step 56 whether the designated medical information belongs to the recording area $D_4$ for image file and the like. If YES, recording of corresponding image information is needed and the procedure proceeds to step 57. In step 57, the image information from the imaging unit 5 is temporarily stored in a memory built in the processor and in step 58, a vacant area in the recording area corresponding to examination images is searched so that the image information stored in the memory can be recorded on the vacant area in step 59.

When the above operation is terminated, it is decided in step 60 whether the write operation is completed. If completion is determined, the procedure ends but if write data still remain, the procedure returns to step 51. If it is decided in step 56 that the selected medical information does not belong to $D_4$, recording of the image information is unnecessary and NO is issued to cause the procedure to skip over to step 60.

Figure 10:
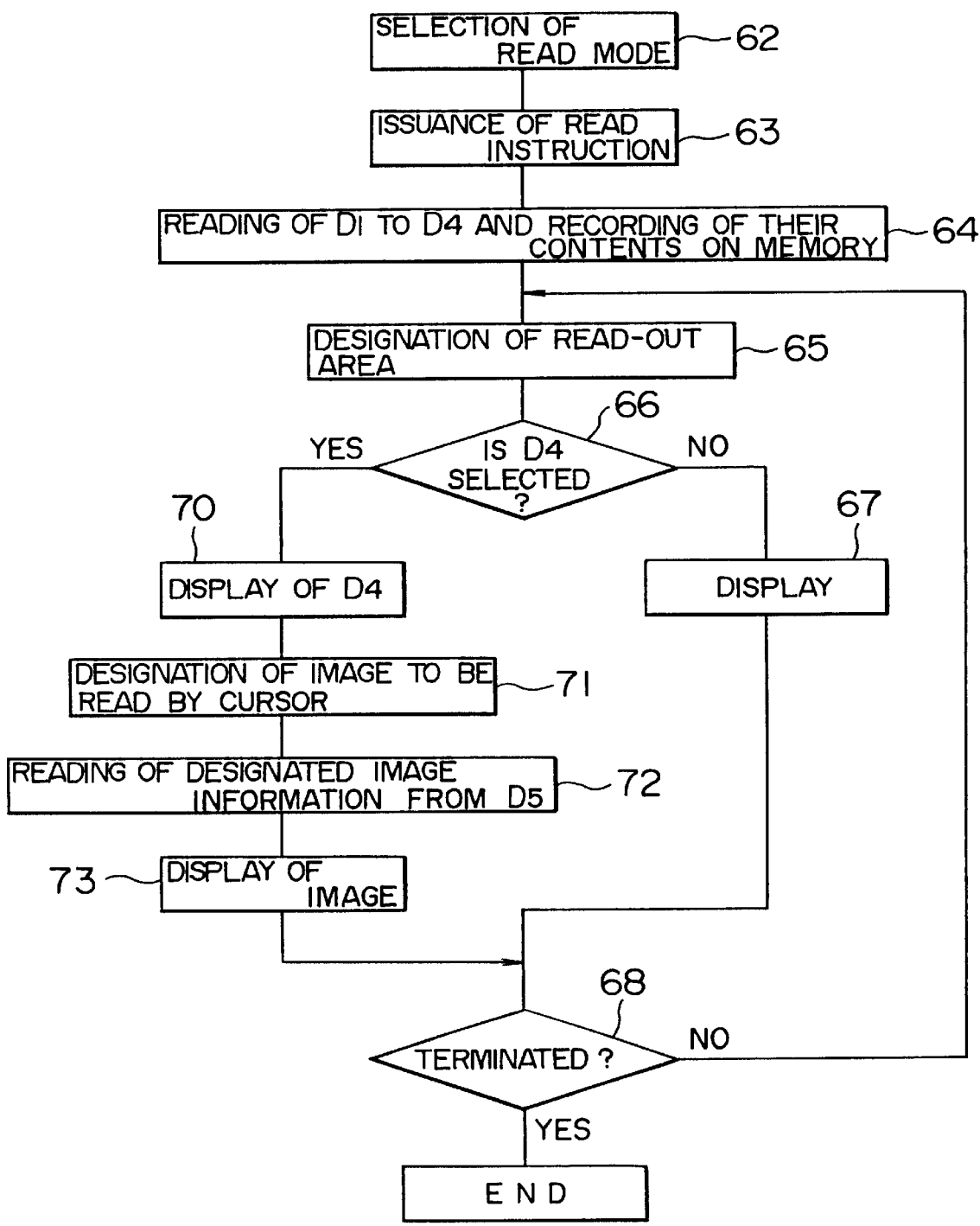
FIG. 10 is a flow chart for explaining the operation of the read mode in accordance with the invention.

When information is read out of the DAT, the processor 2 operates in accordance with an operational flowchart as shown in FIG. 10.

When the read mode is first selected by the input/output unit 1 in step 62, a read instruction is issued in step 63 and the contents of the areas $D_1$ to $D_4$ of the DAT is recorded on the memory of the processor 2 in step 64. Subsequently, in step 65, the headings of medical information are displayed and the desired kind of medical information is designated by the cursor. In step 66, it is decided whether the designated medical information is the medical information $D_4$ about image file and the like. If NO, the designated medical information is read out of the memory and displayed on the display unit 4 in step 67. It is decided in step 68 whether reading of necessary information is terminated and if YES, the procedure ends. If NO, the procedure returns to step 65 to read new information.

If YES is issued in step 66 to indicate that reading of image information is requested, the contents of the medical information $D_4$ about image file and the like is first read out of the memory and displayed on the display unit 4 in step 70. Subsequently, in step 71, the cursor is moved to designate, on the basis of the displayed information, an image to be read, and the designated image information is read out of the area D5 of the DAT in step 72 and displayed on the display unit 4 in step 73. Then, the procedure proceeds to step 68 where the same operation as described previously is performed.

As described above, according to the invention, both the digital information about personal medical history ($D_2$, $D_3$) and digital information about examination image ($D_5$) of individual patients can systematically be recorded on and reproduced from the recording medium in the form of the DAT by using the DAT unit 3. Specifically, in actually conducting diagnosis and therapy in hospitals, not only the personal medical history of individual patients but also various examination images of individual patients can be taken out of a roll of the DAT. Accordingly, sufficient diagnostic information can be obtained rapidly to permit the patient to receive efficient diagnostic and therapeutic treatments. Further, duplicative examination of the same diagnostic part which has been imaged in the past to provide an examination image can be avoided to thereby prevent an unnecessary load from being imposed on the patient. In addition, the cassette DAT is compact and it can be easy to handle for the purpose of personal management by individual patients and suitable for portability.

What is claimed is:

1. In a medical information recording and reproducing apparatus having a processor connected to an input/output unit, a medical diagnostic imaging unit, a display unit and a digital audio tape (DAT) unit using a digital audiotape cassette including a DAT having a recording area for recording and reproducing digitized audio signals, a method of forming and using a personal medical information file, comprising the steps of:

(a) dividing said recording area of said DAT into a plurality of areas including an identification information (ID) area for storing said ID information of a single specified person, a personal medical history information area for storing case and therapeutic history information of said single specified person, a medicative history information area for storing medicative history information of said single specified person, an examination image history information area and an examination image information area for storing examination image information of said single specified person;

(b) processing medical information including ID information, case and therapeutic history information, medicative history information and examination image history information of said single specified person and examination image information of said specified person received from said input/output unit and said medical diagnostic imaging unit respectively to prepare said information for recording in said DAT;

(c) recording in said ID area of said DAT said ID information of said single specified person and recording data of at least one of said case and therapeutic history information, said medicative history information, said examination image history information and said examination images information, related to a medical treatment said single specified person has received in one of said ID areas, said personal medical history information area, said medicative history information area, said examination image history information area and said examination image information area corresponding to said data to be recorded thereby forming a personal medical information file; and (d) reproducing said personal information file of said single specified person from said DAT when said single specified person is being diagnosed.

2. A method according to claim 1, wherein said recording step further including steps of:

deciding whether said one to be recorded belongs to said examination image history information area; and recording an examination image information relating to said one to be recorded in said examination image information area, when said deciding step decides that said one to be recorded belongs to said examination image history information area.

3. A method according to claim 2, wherein said reproducing step including steps:

displaying on said display unit information recorded in a designated one of said ID area, said personal medical history information are, said medicative history information area and said examination image history information area;

judging whether said designated one is said examination image history information area;

designating an examination image information to be read which is recorded in said examination image history information area, on the basis of the displayed information, when said judging step decides that said designated one is said examination image history information area; and displaying said designated examination image information to be read on said display unit.

4. In a medical information recording and reproducing apparatus having a processor connected to an input/output unit, a medical diagnostic imaging unit, a display unit and a digital audio tape (DAT) unit using a digital audiotape cassette including a DAT having a recording area for recording and reproducing digitized audio signals a method of forming and using a personal medical information file comprising the steps of:

(a) dividing said recording area of said DAT into a plurality of areas including an identification (ID) information area for storing said ID information of a single specified person, a personal medical history information area for storing case and therapeutic history information of said single specified person, a medicative history information area for storing medicative history information of said single specified person, an examination image history information area and an examination image information area for storing examination image information of said single specified person;

(b) processing medical information including ID information, case and therapeutic history information, medicative history information and examination image history information of said single specified person and examination image information of said specified person received from said input/output unit and said medical diagnostic imaging unit respectively to prepare said information for recording in said DAT;

(c) recording in said ID area of said DAT said ID information of said single specified person, and recording data of at least one of said case and therapeutic history information, said medicative history information, said examination image history information and said examination image information, related to a medical treatment said single specified person has received in one of said ID areas, said personal medical history information area, said medicative history information area, said examination image history information area and said examination image information area corresponding to said data to be recorded thereby forming a personal medical information file;

(d) keeping in custody of said single specified person said single DAT cassette recording of said personal medical information file; and (e) reproducing said personal medical information file of said single specified person from said single DAT cassette when said single specified person is being diagnosed.

5. A method according to claim 4, wherein said personal medical history information is character information including letter, numerals and marks and wherein said examination image information includes quantized image information and wherein said personal medical history information and said examination image information are recorded in said DAT cassette in a predetermined format.

6. A method according to claim 4, wherein said personal medical history information and said examination image information obtained each time said single specified person is diagnosed or examined are recorded in said DAT cassette and added to said personal medical information file.

7. A method according to claim 4, wherein said step of keeping in custody of said specified person said DAT cassette recording of said personal medical information file is attained by putting said DAT cassette including said DAT under personal management of said single specified person.

8. A method according to claim 4, wherein said step of keeping in custody of said single specified person said DAT cassette recording of said personal medical information file is attained by putting said DAT cassette including said DAT under personal management of said single specified person each time after said single specified person is diagnosed and personal medical history information and examination image information is added to said personal medical information file.

9. In a medical information recording and reproducing apparatus having a processor connected to an input/output unit, a medical diagnostic imaging unit, a display unit and a digital audio tape (DAT) unit using a digital audiotape cassette including a DAT having a recording area for recording and reproducing digitized audio signals, a method of forming and using a personal medical information file comprising the steps of:

(a) dividing said recording area of said DAT into a plurality of areas including an identification (ID) information area for storing ID information of a single specified person, a personal medical history information area for storing case and therapeutic history information of said single specified person, a medicative history information area for storing said medicative history information of said single specified person, an examination image history information area and an examination image information area for storing examination image information of said single specified person;

(b) formatting, by use of said input/output unit, a personal medical information file which includes medical information having ID information, case and therapeutic history information, medicative history information and examination image history information of said single specified person and said examination image information of said single specified person;

(c) converting said medical information into digitized character data in a format for recording said medical information in said DAT cassette;

(d) converting said examination image information into image data having a format for recording said examination image information in said DAT cassette;

(e) processing said image data and said digitized character data so that said data may be systematically recorded;

(f) recording in said ID area of said DAT said processed digitized character data representing said ID information of said single specified person, and recording data of at least one of said case and therapeutic history information, said medicative history information, said examination image history information and said processed image data representing said examination image information, related to a medical treatment said single specified person has received in one of said ID areas, said personal medical history information area, said medicative history information area, said examination image history information area and said examination image information area corresponding to said data to be recorded thereby forming a personal medical information file;

(g) adding at least one of new data of medical history information and examination image history information and examination image information in each recording area of said DAT, each time said specified person is being diagnosed;

(h) exchanging said DAT cassette, each time a person to be examined is changed;

(i) keeping in custody said DAT cassette recording of personal medical information relating to said specified person;

(j) loading said DAT unit with said DAT cassette recording of said personal medical information file relating to said single specified person; and (k) reading out required data from said DAT cassette with which said DAT unit is loaded to display said read data by said display unit.

10. A method according to claim 9 wherein
keeping in custody said single DAT cassette recording of only said personal medical information relating to said single specified person is attained by putting said single DAT cassette recording of only said personal medical information relating to said single specified person under personal management of said single specified person.

11. The method recited in claim 9, wherein said identification information area for storing ID information of a single specified person is at least 100 KB in size.

12. The method recited in claim 9, wherein each of said identification information area, said personal medical history information area, said medicative history information area and said examination image history information area is at least 100 KB in size.

13. The method recited in claim 9, wherein said examination image information area for storing examination image information of said single specified person is at least 1.4 GB in size.

14. In a medical information recording and reproducing apparatus having a processor connected to an input/output unit, a medical diagnostic imaging unit, a display unit and a digital audio tape (DAT) unit using a digital audio tape cassette including a DAT having a recording area for recording and reproducing digitized audio signals, a method of forming and using a personal medical information file comprising the steps of:

(a) dividing said recording area of said DAT into a plurality of areas including an identification (ID) information area for storing ID information of a single specified person and an examination image information area for storing examination image information for said single specified person;

(b) formatting, by use of said input/output unit, a personal medical information file which includes medical information having ID information and examination image information for said single specified person;

(c) converting said medical information into digitized character data in a format for recording said medical information in said DAT cassette;

(d) converting said examination image information into image data having a format for recording said examination image information in said DAT cassette;

(e) processing said image data and said digitized character data so that said data may be systematically recorded; and (f) recording in said ID area of said DAT said processed digitized character data representing said ID information of said single specified person, and recording data of at least said processed image data representing said examination image information, related to a medical treatment said single specified person has received in said ID area, said examination image information area corresponding to said data to be recorded thereby forming a personal medical information file.

15. A method according to claim 14, further comprising the steps of:

(g) adding new examination image information in each recording area of said DAT, each time said specified person is diagnosed;

(h) exchanging said DAT cassette, each time a person to be examined is changed;

(i) keeping in custody said DAT cassette recording of personal medical information relating to said single specified person;

(j) loading said DAT unit with said DAT cassette recording of said personal medical information file relating to said single specified person; and (k) reading out required data from said DAT cassette with which said DAT unit is loaded to display said read data by said display unit.

16. A medical information recording and reproducing apparatus having a digital audio tape (DAT) unit using a digital audio tape cassette including a DAT having a recording area for recording and reproducing digitized audio signals, said DAT including a recording area divided into a plurality of areas including an identification information area for storing ID information of a single specified person, a personal medical history information area for storing case and therapeutic history information of said single specified person, a medicative history information area for storing said medicative history information of said single specified person, and examination image history information area and an examination image information area for storing examination image information of said single specified person, said apparatus comprising:

a medical diagnostic imaging unit for generating an image of a medical condition of a single specified person;

an input/output unit for formatting a personal medical information file which includes medical information having ID information, case and therapeutic history information, medicative history information and examination image history information of said single specified person and said examination image information of said single specified person; and a processor for converting said medical information into digitized character data in a format for recording said medical information and said DAT cassette, for converting said examination image information into image data having a format for recording said examination image information in said DAT cassette, and for processing said image data and said digitized character data so that said image data and said digitized character data may be systematically recorded;

means for recording in said ID areas of said DAT said processed digitized character data representing said ID information of said single specified person, and recording data of at least one of said case and therapeutic history information, said medicative history information, said examination image history information, and said processed image data representing said examination image information, related to a medical treatment said single specified person has received in one of said ID areas, said personal medical history information area, said medicative history information area, said examination image history information area and said examination image information area corresponding to said data to be recorded thereby forming a personal medical information file;

means for adding at least one of new data of medical history information and examination image history information and examination image information in each recording area of said DAT, each time said specified person is diagnosed; and means for reading out required data from said DAT cassette with which said DAT unit is loaded to display said read data by said display unit.

17. A medical information recording and reproducing apparatus adapted to receive images from a medical diagnostic imaging unit, said apparatus comprising:

an input/output unit for formatting a personal medical information file which includes medical information having ID information, case and therapeutic history information, medicative history information and examination image history information of said single specified person and said examination image information of said single specified person;

a digital audio tape (DAT) unit using a digital audio tape cassette including a DAT having a recording area for recording and reproducing digitized audio signals, said recording area of said DAT being divided into a plurality of areas including a identification information area for storing ID information of a single specified person, a personal medical history information area for storing case and therapeutic history information of said single specified person, a medicative history information area for storing said medicative history information of said single specified person, an examination image history information area and an examination image information area for storing examination image information of said single specified person;

a processor for converting medical information into digitized character data and a format for recording said medical information in said DAT cassette, for converting said examination image information into image data having a format for recording said examination image information in said DAT cassette, and for processing said image data and said digitized character data so that said data may be systematically recorded, wherein said DAT unit records in said ID areas of said DAT said processed digitized character data representing said ID information of said single specified person, and recording data of at least one of said case and therapeutic history information, said medicative history information, said examination image history information and said processed imaged data representing said examination image information, related to a medical treatment said single specified person has received in one of said ID areas, said personal medical history information area, said medicative history information area, said examination image history information area and said examination image information area corresponding to said data to be recorded thereby forming a personal medical information file, and wherein said DAT unit adds at least one of new data of medical history information and examination image history information and examination image information in each recording area of said DAT, each time said specified person is diagnosed.

18. An apparatus according to claim 17, further comprising:

a medical diagnostic imaging unit for generating an image of a medical condition of a single specified person; and a display unit for displaying data read out from said DAT cassette loaded in said DAT unit.

19. In a medical information recording and reproducing apparatus having a processor connected to an input/output unit, a medical diagnostic imaging unit, a display unit and a digital audio tape (DAT) unit using a digital audio tape cassette including a DAT having a recording area for recording and reproducing digitized audio signals, a method of forming and using a personal medical information file, comprising the steps of:

(a) dividing said recording area of said DAT into a plurality of areas including an identification information (ID) area for storing said ID information of a single specified person, a personal medical history information area for storing case and therapeutic history information of said single specified, a medicative history information area for storing medicative history information of said single specified person, an examination image history information area and an examination image information area for storing examination image information of said single specified person, each of said identification information area, said personal medical history information area, said medicative history information area and said examination image history information area being at least 100 KB in size, and said examination image information area being at least 1.4 GB in size;

(b) processing medical information including ID information, case and therapeutic history information, medicative history information and examination image history information of said single specified person and examination image information of said single specified person received from said input/output and said medical diagnostic imaging unit respectively to prepare said information for recording in said DAT;

(c) recording in said ID area of said DAT said ID information of said single specified person, and recording data of at least one of said case and therapeutic history information, said medicative history information, said examination image history information and said examination images information, related to a medical treatment said single specified person has received in one of said ID areas, said personal medical history information area, said medicative history information area, said examination image history information area and said examination image information area corresponding to said data to be recorded thereby forming a personal medical information file; and (d) reproducing said personal information file of said single specified person from said DAT when said single specified person is diagnosed.

* * * * *